US00RE45616E

(19) United States
(12) Reissued Patent
Barrett et al.

(10) Patent Number: US RE45,616 E
(45) **Date of Reissued Patent: *Jul. 21, 2015**

(54) MULTI-CHANNEL NON-INVASIVE TISSUE OXIMETER

(75) Inventors: Bruce J. Barrett, Birmingham, MI (US); Oleg Gonopolsky, West Bloomfield Township, MI (US); Richard S. Scheuing, Largo, FL (US)

(73) Assignee: COVIDIEN LP, Mansfield, MA (US)

( * ) Notice: This patent is subject to a terminal disclaimer.

(21) Appl. No.: 13/780,326

(22) Filed: Feb. 28, 2013

Related U.S. Patent Documents

Reissue of:

(64) Patent No.: 6,615,065
Issued: Sep. 2, 2003
Appl. No.: 09/807,676
PCT Filed: Oct. 13, 1999
PCT No.: PCT/US99/22940
§ 371 (c)(1),
(2), (4) Date: Jul. 12, 2001
PCT Pub. No.: WO00/21435
PCT Pub. Date: Apr. 20, 2000

U.S. Applications:

(63) Continuation of application No. 11/219,298, filed on Sep. 2, 2005, which is an application for the reissue of Pat. No. 6,615,065.

(60) Provisional application No. 60/103,985, filed on Oct. 13, 1998.

(51) Int. Cl.
*A61B 5/00* (2006.01)
*A61B 5/1455* (2006.01)
*G01J 3/42* (2006.01)

(52) U.S. Cl.
CPC ..... *A61B 5/14553* (2013.01); *A61B 5/6814* (2013.01); *A61B 5/14552* (2013.01); *A61B 2562/04* (2013.01); *A61B 2562/164* (2013.01)

(58) Field of Classification Search
CPC ..... A61B 5/6814; A61B 5/14553; A61B 5/14552; A61B 2562/164; A62B 2562/04
USPC ..... 600/322, 323, 336, 340; 356/319
See application file for complete search history.

(56) References Cited

U.S. PATENT DOCUMENTS

| | | | | | |
|---|---|---|---|---|---|
| 4,281,645 | A | * | 8/1981 | Jobsis | 600/324 |
| 4,321,930 | A | * | 3/1982 | Jobsis et al. | 600/344 |
| 4,510,938 | A | * | 4/1985 | Jobsis et al. | 600/344 |
| 4,570,638 | A | * | 2/1986 | Stoddart et al. | 600/476 |
| 4,725,147 | A | * | 2/1988 | Stoddart | 356/433 |
| 4,768,516 | A | * | 9/1988 | Stoddart et al. | 600/474 |
| 4,817,623 | A | * | 4/1989 | Stoddart et al. | 600/477 |
| 4,910,404 | A | * | 3/1990 | Cho et al. | 250/358.1 |

(Continued)

*Primary Examiner* — Long V Le
*Assistant Examiner* — Angela M Hoffa
(74) *Attorney, Agent, or Firm* — Faegre Baker Daniels LLP

(57) ABSTRACT

A method and apparatus for spectrophotometric in vivo monitoring of blood metabolites such as hemoglobin oxygen concentration at a plurality of different areas or regions on the same organ or test site on an ongoing basis, by applying a plurality of spectrophotometric sensors to a test subject at each of a corresponding plurality of testing sites and coupling each such sensor to a control and processing station, operating each of said sensors to spectrophotometrically irradiate a particular region within the test subject; detecting and receiving the light energy resulting from said spectrophotometric irradiation for each such region and conveying corresponding signals to said control and processing station, analyzing said conveyed signals to determine preselected blood metabolite data, and visually displaying the data so determined for each of a plurality of said areas or regions in a comparative manner.

23 Claims, 10 Drawing Sheets

(56) References Cited

U.S. PATENT DOCUMENTS

| | | | | | |
|---|---|---|---|---|---|
| 5,088,493 | A | * | 2/1992 | Giannini et al. | 600/323 |
| 5,139,025 | A | * | 8/1992 | Lewis et al. | 600/477 |
| 5,140,989 | A | * | 8/1992 | Lewis et al. | 600/476 |
| 5,190,039 | A | * | 3/1993 | Takeuchi et al. | 600/311 |
| 5,217,013 | A | * | 6/1993 | Lewis et al. | 600/342 |
| 5,465,714 | A | * | 11/1995 | Scheuing | 600/323 |
| 5,477,853 | A | * | 12/1995 | Farkas et al. | 600/310 |
| 5,482,034 | A | * | 1/1996 | Lewis et al. | 600/323 |
| 5,537,209 | A | * | 7/1996 | Lis | 356/487 |
| 5,539,201 | A | * | 7/1996 | Liva et al. | 250/227.21 |
| 5,542,421 | A | * | 8/1996 | Erdman | 600/477 |
| 5,584,296 | A | * | 12/1996 | Cui et al. | 600/479 |
| 5,661,302 | A | * | 8/1997 | Evans et al. | 250/339.12 |
| 5,697,367 | A | * | 12/1997 | Lewis et al. | 600/310 |
| 5,779,631 | A | * | 7/1998 | Chance | 600/328 |
| 5,787,887 | A | * | 8/1998 | Klingenbeck-Regn | 600/407 |
| 5,803,909 | A | * | 9/1998 | Maki et al. | 600/310 |
| 5,853,370 | A | * | 12/1998 | Chance et al. | 600/473 |
| 5,873,821 | A | * | 2/1999 | Chance et al. | 600/310 |
| 5,902,235 | A | * | 5/1999 | Lewis et al. | 600/323 |
| 5,954,053 | A | * | 9/1999 | Chance et al. | 600/310 |
| 5,974,337 | A | * | 10/1999 | Kaffka et al. | 600/316 |
| 5,987,351 | A | * | 11/1999 | Chance | 600/473 |
| 6,128,517 | A | * | 10/2000 | Maki et al. | 600/310 |
| 6,240,309 | B1 | * | 5/2001 | Yamashita et al. | 600/407 |
| 6,282,438 | B1 | * | 8/2001 | Maki et al. | 600/476 |
| 6,334,065 | B1 | * | 12/2001 | Al-Ali et al. | 600/323 |
| 6,397,099 | B1 | * | 5/2002 | Chance | 600/473 |
| 6,549,795 | B1 | * | 4/2003 | Chance | 600/340 |
| 6,615,065 | B1 | * | 9/2003 | Barrett et al. | 600/340 |
| RE44,735 | E | * | 1/2014 | Barrett et al. | 600/322 |

* cited by examiner

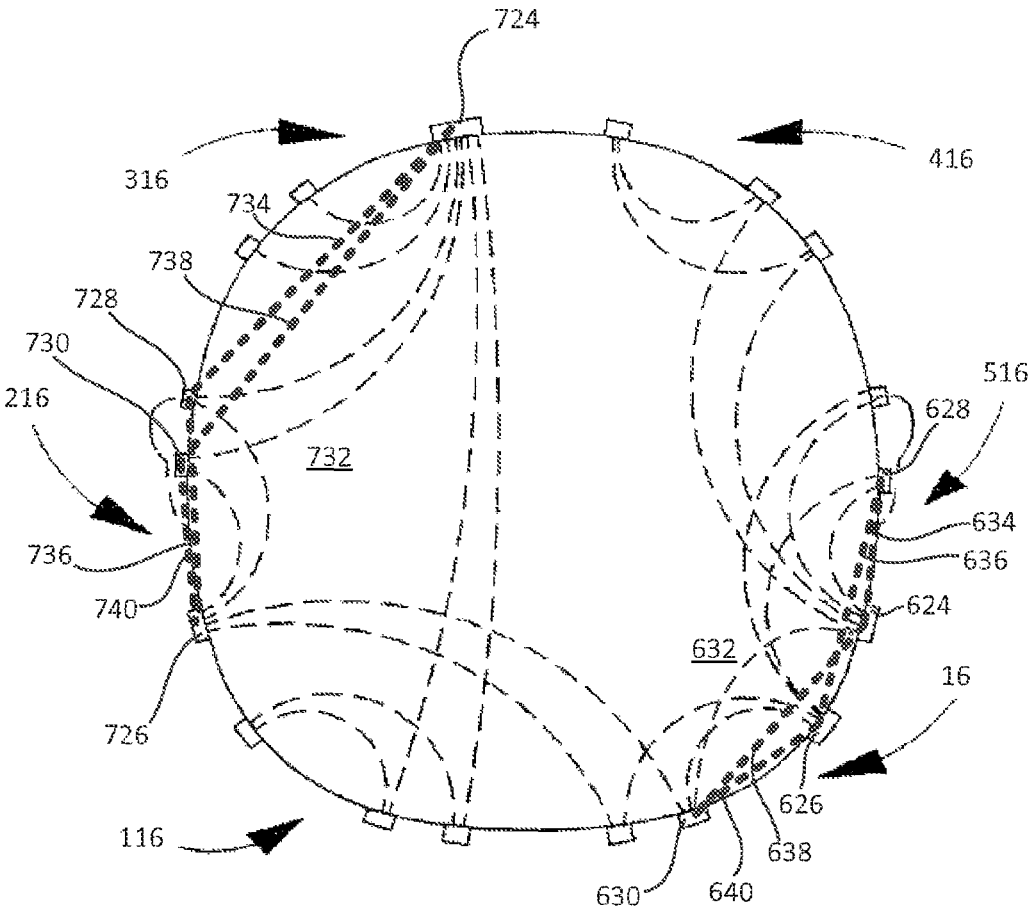
FIG. 11
NEW

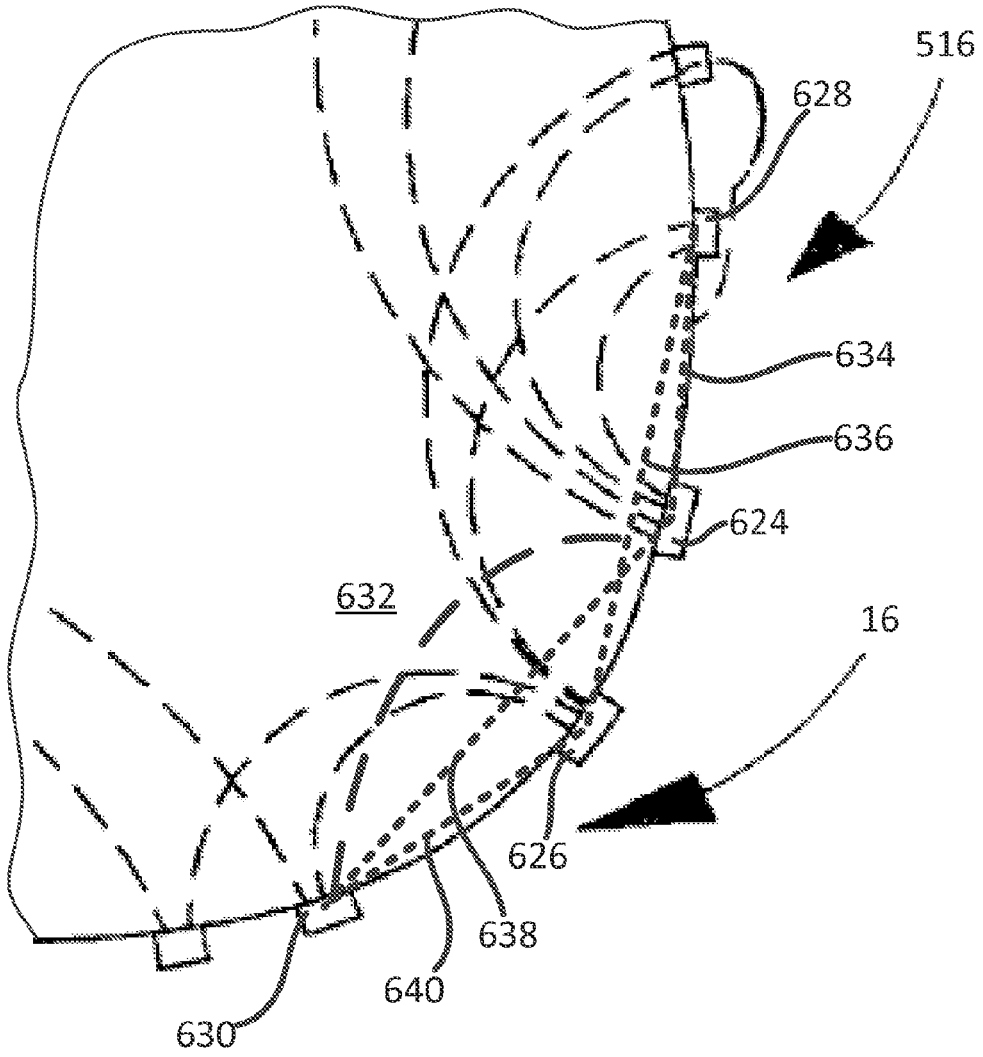
FIG. 12
NEW

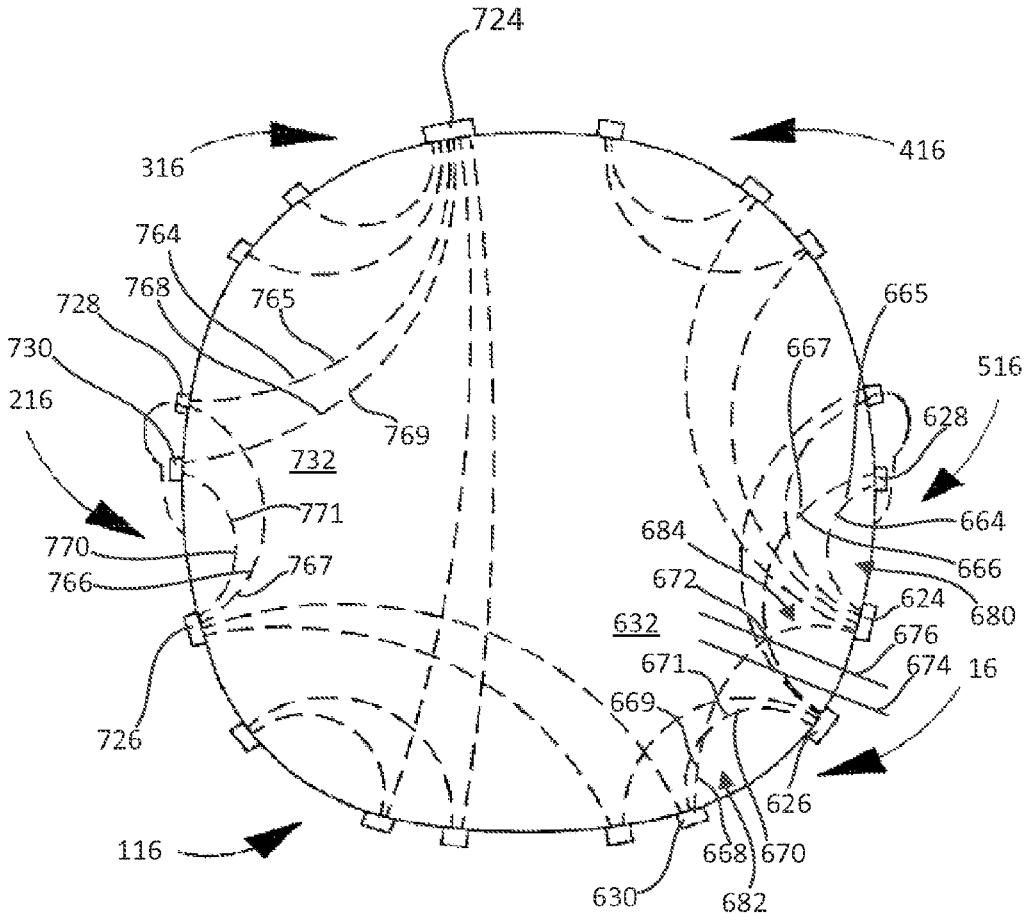
FIG. 13
NEW

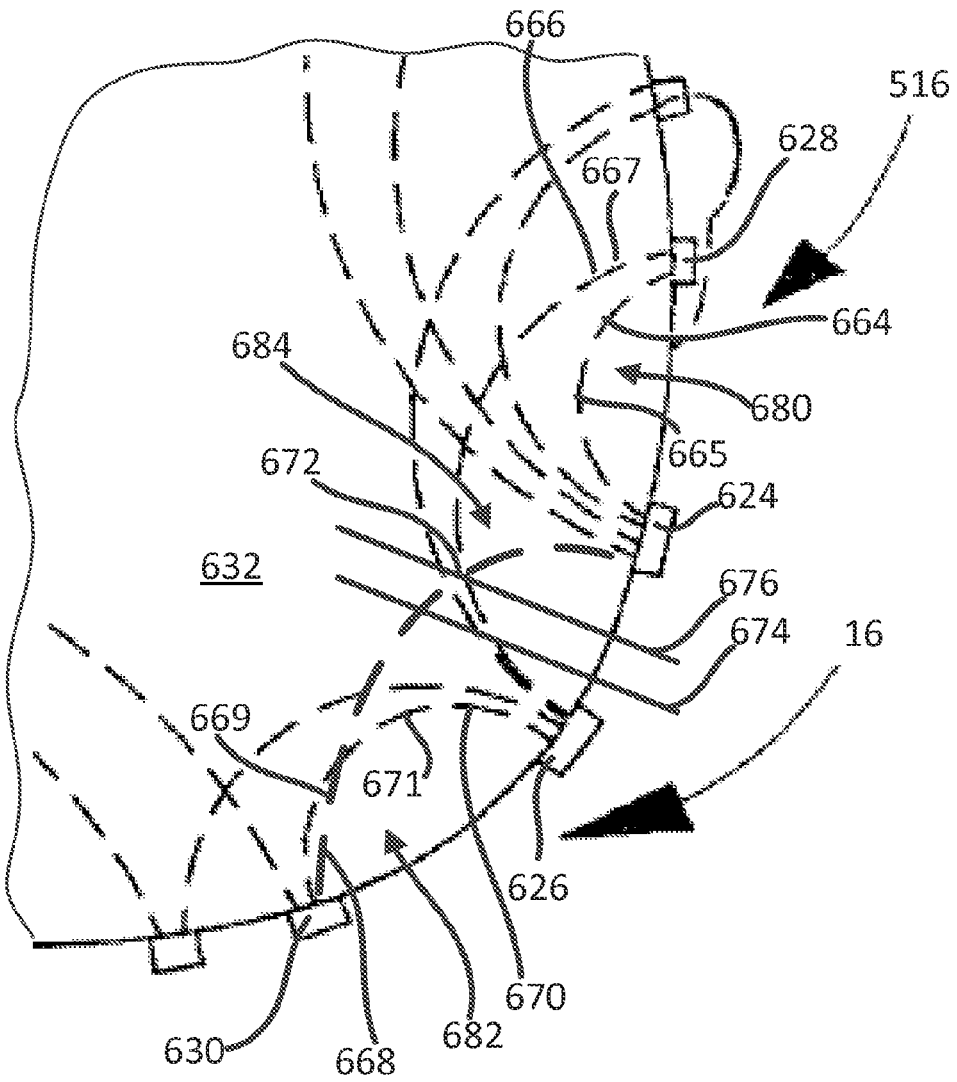
FIG. 14
NEW

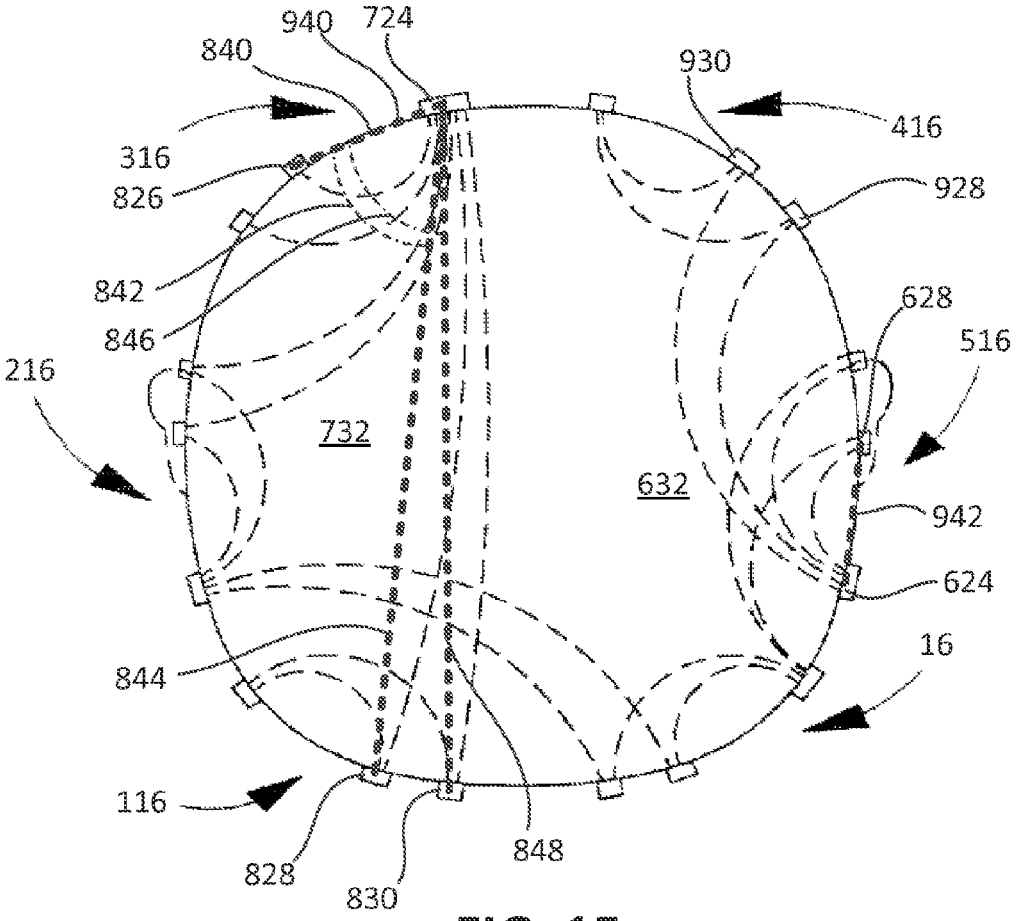
FIG. 15
NEW

MULTI-CHANNEL NON-INVASIVE TISSUE OXIMETER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 6,615,065. Reissue application Ser. No. 11/219,298 was previously filed for the reissue of U.S. Pat. No. 6,615,065. The present application is a Continuation Reissue Application of Reissue application Ser. No. 11/219,298. Three other Continuation Reissue Applications of Reissue application Ser. No. 11/219,298 are filed on the same day as this Continuation Reissue Application, specifically, Continuation Reissue application Ser. No. 13/780,269, Continuation Reissue application Ser. No. 13/780,300, and Continuation Reissue application Ser. No. 13/780,314, all having the same title and same inventors as U.S. Pat. No. 6,615,065.*

*CROSS REFERENCE TO RELATED APPLICATIONS*

[This application is a national stage of International Application No. PCT/US99/22940, filed Oct. 13, 1999, which claims the benefit of U.S. Provisional Application Ser. No. 60/103,985, filed Oct. 13, 1998.]

*This application is a Continuation Reissue Application of Reissue application Ser. No. 11/219,298, which was filed for the reissue of U.S. Pat. No. 6,615,065, which is a national stage of International Application No. PCT/US99/22940, filed Oct. 13, 1999, which claims the benefit of U.S. Provisional Application Ser. No. 60/103,985, filed Oct. 13, 1998.*

This invention relates generally to in vivo spectrophotometric examination and monitoring of selected blood metabolites or constituents in human and/or other living subjects, e.g., medical patients, and more particularly to spectrophotometric oximetry, by transmitting selected wavelengths (spectra) of light into a given area of the test subject, receiving the resulting light as it leaves the subject at predetermined locations, and analyzing the received light to determine the desired constituent data based on the spectral absorption which has occurred, from which metabolic information such as blood oxygen saturation may be computed for the particular volume of tissue through which the light spectra have passed.

A considerable amount of scientific data and writings, as well as prior patents, now exist which is/are based on research and clinical studies done in the above-noted area of investigation, validating the underlying technology and describing or commenting on various attributes and proposed or actual applications of such technology. One such application and field of use is the widespread clinical usage of pulse oximeters as of the present point in time, which typically utilize sensors applied to body extremities such as fingers, toes, earlobes, etc., where arterial vasculature is in close proximity, from which arterial hemoglobin oxygenation may be determined non-invasively. A further and important extension of such technology is disclosed and discussed in U.S. Pat. No. 5,902,235, which is related to and commonly owned with the present application and directed to a non-invasive spectrophotometric cerebral oximeter, by which blood oxygen saturation in the brain may be non-invasively determined through the use of an optical sensor having light emitters and detectors that is applied to the forehead of the patient. Earlier patents commonly owned with the '235 patent and the present one pertaining to various attributes of and applications for the underlying technology include U.S. Pat. Nos. 5,139,025; 5,217,013; 5,465,714; 5,482,034; and 5,584,296.

The cerebral oximeter of the aforementioned '235 patent has proved to be an effective and highly desirable clinical instrument, since it provides uniquely important medical information with respect to brain condition (hemoglobin oxygen saturation within the brain, which is directly indicative of the single most basic and important life parameter, i.e. brain vitality). This information was not previously available, despite its great importance, since there really is no detectable arterial pulse within brain tissue itself with respect to which pulse oximetry could be utilized even if it could be effectively utilized in such an interior location (which is very doubtful), and this determination therefore requires a substantially different kind of apparatus and determination analysis. In addition, there are a number of uniquely complicating factors, including the fact that there is both arterial and venous vasculature present in the skin and underlying tissue through which the examining light spectra must pass during both entry to and exit from the brain, and this would distort and/or obscure the brain examination data if excluded in some way. Furthermore, the overall blood supply within the skull and the brain itself consists of a composite of arterial, venous, and capillary blood, as well as some pooled blood, and each of these are differently oxygenated. In addition, the absorption and scatter effects on the examination light spectra are much greater in the brain and its environment than in ordinary tissue, and this tends to result in extremely low-level electrical signal outputs from the detectors for analysis, producing difficult signal-to-noise problems.

Notwithstanding these and other such problems, the cerebral oximeter embodying the technology of the aforementioned issued patents (now available commercially from Somanetics Corporation, of Troy, Mich.) has provided a new type of clinical instrument by which new information has been gained relative to the operation and functioning of the human brain, particularly during surgical procedures and/or injury or trauma, and this has yielded greater insight into the functioning and state of the brain during such conditions. This insight and knowledge has greatly assisted surgeons performing such relatively extreme procedures as carotid endarterectomy, brain surgery, and other complex procedures, including open-heart surgery, etc. and has led to a greater understanding and awareness of conditions and effects attributable to the hemispheric structure of the human brain, including the functional inter-relationship of the two cerebral hemispheres, which are subtly interconnected from the standpoint of blood perfusion as well as that of electrical impulses and impulse transfer.

BRIEF SUMMARY OF INVENTION

The present invention results from the new insights into and increased understanding of the human brain referred to in the preceding paragraph, and provides a methodology and apparatus for separately (and preferably simultaneously) sensing and quantitatively determining brain oxygenation at a plurality of specifically different locations or regions of the brain, particularly during surgical or other such traumatic conditions, and visually displaying such determinations in a directly comparative manner. In a larger sense, the invention may also be used to monitor oxygenation (or other such metabolite concentrations or parameters) in other organs or at other body locations, where mere arterial pulse oximetry is a far too general and imprecise examination technique.

Further, and of considerable moment, the invention provides a method and apparatus for making and displaying determinations of internal metabolic substance, as referred to in the preceding paragraph, at a plurality of particular and differing sites, and doing so on a substantially simultaneous and continuing basis, as well as displaying the determinations for each such site in a directly comparative manner, for immediate assessment by the surgeon or other attending clinician, on a real-time basis, for direct support and guidance during surgery or other such course of treatment.

In a more particular sense, the invention provides a method and apparatus for spectrophotometric in vivo monitoring of blood metabolites such as hemoglobin oxygen concentration in any of a preselected plurality of different regions of the same test subject and on a continuing and substantially instantaneous basis, by applying a plurality of spectrophotometric sensors. In a more particular sense, the invention provides a method and apparatus for spectrophotometric in vivo monitoring of blood metabolites such as hemoglobin oxygen concentration in any of a preselected plurality of different regions of the same test subject and on a continuing and substantially instantaneous basis, by applying a plurality of spectrophotometric sensors to the test subject at each of a corresponding plurality of testing sites, coupling each such sensor to a control and processing station, operating each such sensor to spectrophotometrically irradiate a particular region within the test subject associated with that sensor, detecting and receiving the light energy resulting from such spectrophotometric irradiation for each such region, conveying signals corresponding to the light energy so received to the control and processing station, analyzing the conveyed signals to determine preselected blood metabolite data, and displaying the data so obtained from each of a plurality of such testing sites and for each of a plurality of such regions, in a region-comparative manner.

The foregoing principal aspects and features of the invention will become better understood upon review of the ensuing specification and the attached drawings, describing and illustrating preferred embodiments of the invention.

BRIEF DESCRIPTION OF THE DRAWINGS

*FIG. 11 is the pictorialized cross-sectional view of FIG. 10 with annotations identifying particular optical elements, as well as their spacing and relationships;*

*FIG. 12 is an enlarged view of the cross-sectional view of FIG. 11 that depicts the spacing and relationships for some of the identified optical elements;*

*FIG. 13 is the pictorialized cross-sectional view of FIG. 10 with annotations identifying particular optical elements, as well as their spacing and mean paths;*

*FIG. 14 is an enlarged view of the cross-sectional view of FIG. 13 that depicts the spacing and mean paths for some of the identified optical elements; and*

*FIG. 15 is the pictorialized cross-sectional view of FIG. 10 with annotations identifying particular optical elements, as well as their spacing and relationships.*

DESCRIPTION OF PREFERRED EMBODIMENT

Figure 1:
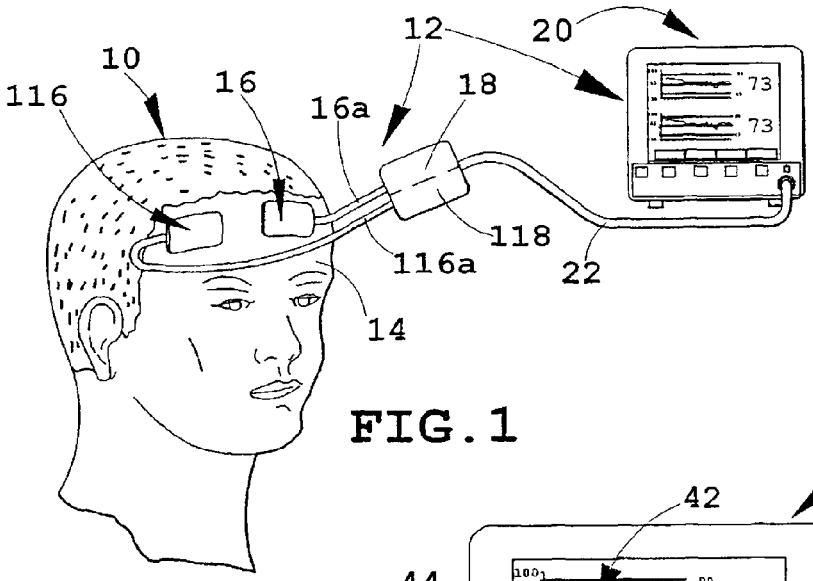
FIG. 1 is a pictorial representation of a patient on whom apparatus in accordance with the invention is being used.

FIG. 1 depicts an illustrative patient 10 on whom an instrument 12 in accordance with the present invention is being employed. As illustrated, the forehead 14 of patient 10 has a pair of sensors 16, 116 secured to it in a bilateral configuration, i.e., one such sensor on each side of the forehead, where each may monitor a different brain hermisphere. Each of the sensors 16, 116 is connected to a processor and display unit 20 which provides a central control and processing station (sometimes hereinafter, referred to as the "oximeter") by a corresponding electrical cable 16A, 116A, which join one another at a dual-channel coupler/pre-amp 18, 118 and then (preferably) proceed to the control and processor 20 as an integrated, multiple-conductor cable 22. As will be understood, the electrical cables just noted include individual conductors for energizing light emitters and operating the related light detectors contained in sensors 16, 116, all as referred to further hereinafter and explained in detail in the various prior patents.

Figure 2:
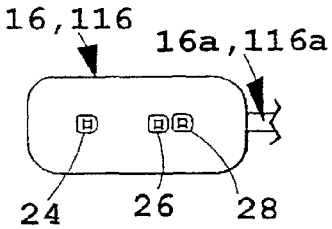
FIG. 2 is a fragmentary plan view of a typical sensor used in accordance with the invention.

The general nature of a typical structure and arrangement for the sensors 16,116 (which are identical in nature and which may if desired be incorporated into a single physical unit) is illustrated in FIG. 2, and comprises the subject matter of certain of the earlier patents, in particular U.S. Pat. Nos. 5,465,714; 5,482,034; 5,584,296; and 5,795,292, wherein the structure and componentry of preferred sensors are set forth in detail. For present purposes, it is sufficient to note that the sensors 16, 116 include an electrically actuated light source 24 for emitting the selected examination spectra (e.g., two or more narrow-bandwidth LEDs, whose center output wavelengths correspond to the selected examination spectra), together with a pair of light detectors 26, 28 (e.g., photodiodes) which are preferably located at selected and mutually different distances from the source 24. These electro-optical (i.e., "optode") components are precisely positioned upon and secured to, or within, a sensor body having a foam or other such soft and conformable outer layer which is adhesively secured to the forehead (or other desired anatomical portion) of the patient 10, as generally illustrated in FIG. 1, and individual electrical conductors in cables 16A, 116A provide operating power to the sources 24 while others carry output signals from the detectors 26, 28, which are representative of detected light intensities received at the respective detector locations and must be conveyed to the processor unit 20, where processing takes place.

Figure 3:
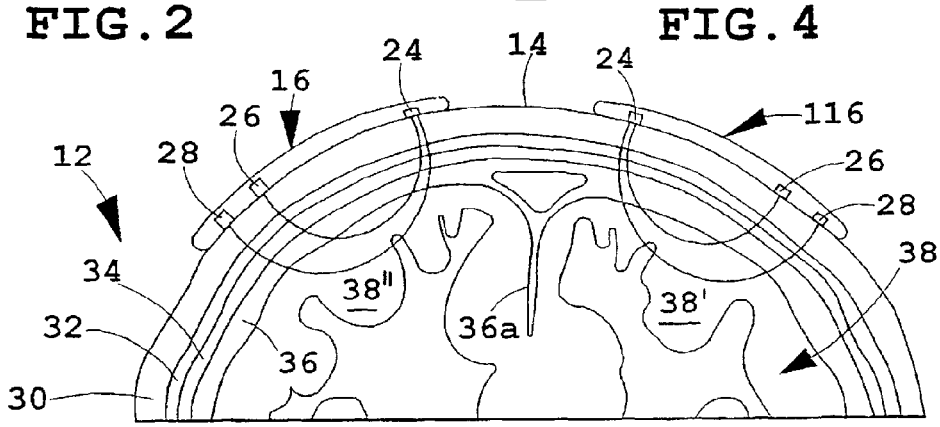
FIG. 3 is an enlarged, fragmentary, pictorial cross-sectional view of a human cranium, showing the sensors of FIG. 2 applied and in place, generally illustrating both structural and functional aspects of the invention.

FIG. 3 generally illustrates, by way of a pictorialized cross-sectional view, the sensors 16, 116 in place upon the forehead 14 of the patient 12. As illustrated in this figure, the cranial structure of patient 12 generally comprises an outer layer of skin 30, an inner layer of tissue 32, and the frontal shell 34 of the skull, which is of course bone.

Inside the skull 34 is the Periosteal Dura Mater, designated by the numeral 36, and inside that is the brain tissue 38 itself, which is comprised of two distinct hemispheres 38', 38" that are separated at the center of the forehead inwardly of the superior sagital sinus by a thin, inwardly-projecting portion 36a of the Dura 36. Thus, in the arrangement illustrated in FIG. 3, sensor 16 accesses and examines brain hemisphere 38", while sensor 116 does the same to brain hemisphere 38'.

As explained at length in various of the above-identified prior patents, the preferred configuration of sensors 16, 116 includes both a "near" detector 26, which principally receives light from source 24 whose mean path length is primarily confined to the layers of skin, tissue, skull, etc., outside brain 38, and a "far" detector 28, which receives light spectra that have followed a longer mean path length and traversed a substantial amount of brain tissue in addition to the bone and tissue traversed by the "near" detector 26. Accordingly, by appropriately differentiating the information from the "near" (or "shallow") detector 26 (which may be considered a first data set) from information obtained from the "far" (or "deep") detector 28 (providing a second such data set), a resultant may be obtained which principally characterizes conditions within the brain tissue itself, without effects attributable to the overlying adjacent tissue, etc. This enables the apparatus to obtain metabolic information on a selective basis, for particular regions within the test subject, and by spectral analysis of this resultant information, employing appropriate extinction coefficients, etc. (as set forth in certain of the above-identified patents), a numerical value, or relative quantified value, may be obtained which characterizes metabolites or other metabolic data (e.g., the hemoglobin oxygen saturation) within only the particular region or volume of tissue actually examined, i.e., the region or zone generally defined by the curved mean path extending from source 24 to the "far" or "deep" detector 28, and between this path and the outer periphery of the test subject but excluding the analogous region or zone defined by the mean path extending from source 24 to "near" detector 26. As will be understood, particularly in view of Applicants' above-identified prior patents as well as is explained further hereinafter, this data analysis carried out by the "control and processing unit" 20 is accomplished by use if an appropriately programmed digital computer, as is now known by those skilled in the art (exemplified in particular by the Somanetics® model 4100 cerebral oximeter).

The present invention takes advantage of the primarily regional oxygen saturation value produced by each of the two (or more) sensors 16, 116, together with the natural hemispheric structure of brain 38, by use of a comparative dual or other multi-channel examination paradigm that in the preferred embodiment or principal example set forth herein provides a separate but preferably comparatively displayed oxygen saturation value for each of the two brain hemispheres 38', 38". Of course, it will be understood that each such regional index or value of oxygen saturation is actually representative of the particular region within a hemisphere actually subjected to the examining light spectra, and while each such regional value may reasonably be assumed to be generally representative of the entire brain hemisphere in which it is located, and therefor useful in showing and contrasting the differing conditions between the two such hemispheres of the brain 38, the specific nature and understanding of these hemispheric interrelationships and of interrelationships between other and different possible sensor locations relative to each different hemisphere 38', 38" are not believed to be fully known and appreciated as of yet. Consequently, it may be useful or advantageous in at least some cases, and perhaps in many, to employ a more extensive distribution and array of sensors and corresponding inputs to the oximeter 20, such as is illustrated for example in FIG. 8.

Figure 8:
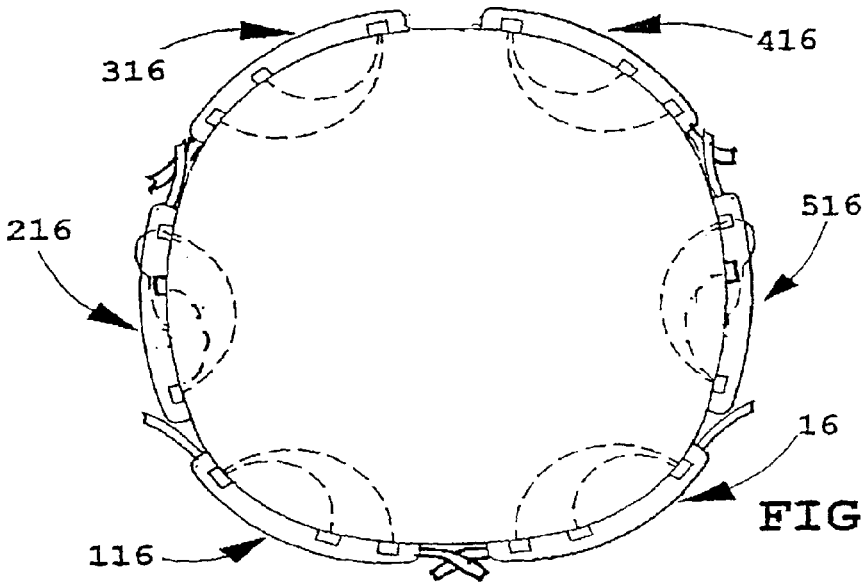
FIG. 8 is a pictorialized cross-sectional view representing a test subject on which a multiplicity of sensors are placed in sequence, further illustrating the multi-channel capability of the present invention.

Thus, as seen in FIG. 8, a more extensive array of sensors 16, 116, 216, etc., may be deployed around the entire circumference of the head or other such patient extremity, for example, each such sensor sampling a different regional area of each brain hemisphere or other such organ or test site and outputting corresponding data which may be contrasted in various ways with the analogous data obtained from the other such sensors for other test site regions. In this regard, it will be appreciated that the extent of each such regional area subjected to examination is a function of a number of different factors, particularly including the distance between the emitter or source 24 and detectors 26, 28 of each such set and the amount of light intensity which is utilized, the greater the emitter/sensor distance and corresponding light intensity, the greater the area effectively traversed by the examining light spectra and the larger the size of the "region" whose oximetric or other metabolic value is being determined.

It may also be possible to use only a single source position and employ a series of mutually spaced detector sets, or individual detectors, disposed at various selected distances from the single source around all or a portion of the perimeter of the subject. Each such single source would actually illuminate the entire brain since the photons so introduced would scatter throughout the interior of the skull (even though being subject to increased absorption as a function of distance traversed), and each such emitter/detector pair (including long-range pairs) could produce information characterizing deeper interior regions than is true of the arrays illustrated in FIGS. 3 and 8, for example. Of course, the smaller-region arrays shown in these figures are desirable in many instances, for a number of reasons. For example, the comparative analysis of information corresponding to a number of differing such regions, as represented by the array of FIG. 8, lends itself readily to very meaningful comparative displays, including for example computer-produced mapping displays which (preferably by use of differing colors and a color monitor screen) could be used to present an ongoing real-time model which would illustrate blood or even tissue oxygenation state around the inside perimeter of and for an appreciable distance within a given anatomical area or part. The multiple detector outputs from such a single-source arrangement, on the other hand, would contain information relative to regions or areas deep within the brain, and might enable the determination of $rSO_2$ values (or other parameters) for deep internal regions as well as the production of whole-brain mapping, by differentially or additively combining the outputs from various selected detectors located at particular points.

The dual or bilateral examination arrangement depicted in FIGS. 1 and 3 will provide the highly useful comparative display formats illustrated in FIGS. 4, 5, 6, and 7 (as well as on the face of the oximeter 20 shown at the right in FIG. 1), for example. In the arrangement shown in FIGS. 1 and 4, each sensor output is separately processed to provide a particular regional oxygen saturation value, and these regional values are separately displayed on a video screen 40 as both a numeric or other such quantified value, constituting a basically instantaneous real-time value, and as a point in a graphical plot 42, 44, representing a succession of such values taken over time. As illustrated, the plots or graphs 42, 44 may advantageously be disposed one above the other in direct alignment, for convenient examination and comparison.

While the instantaneous numeric displays will almost always be found useful and desirable, particularly when arranged in the directly adjacent and immediately comparable manner illustrated, the graphical trace displays 42, 44 directly show the ongoing trend, and do so in a contrasting, comparative manner, as well as showing the actual or relative values, and thus are also highly useful.

Figure 5:
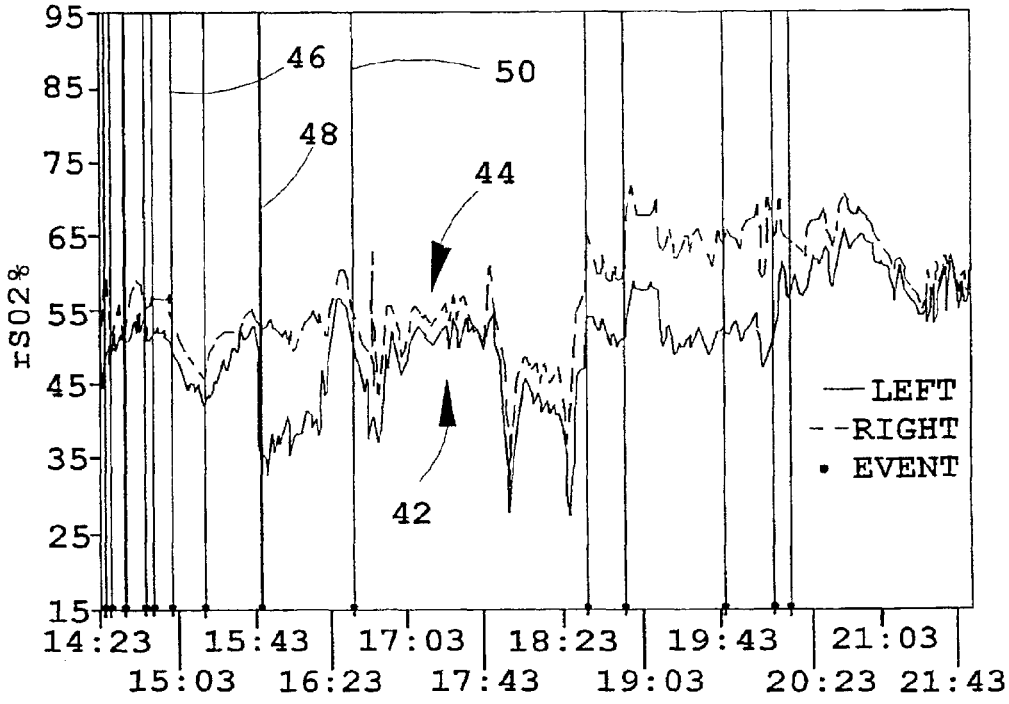
FIGS. 5, 6, and 7 are graphs representing data displays obtained in accordance with the invention which represent actual surgical procedure results from actual patients.
Figure 6:
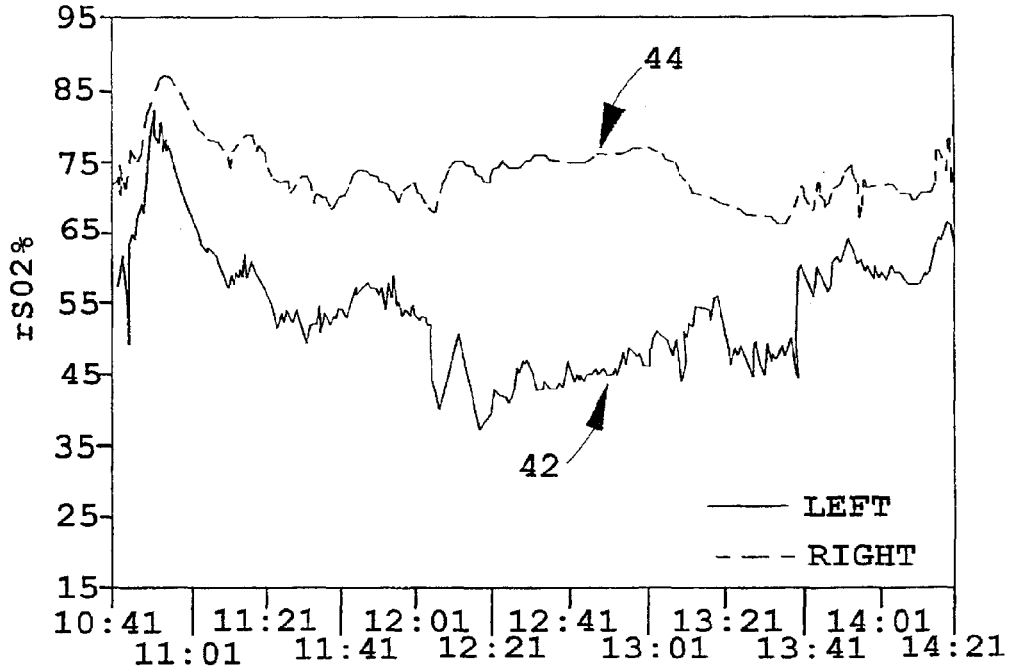
Figure 7:
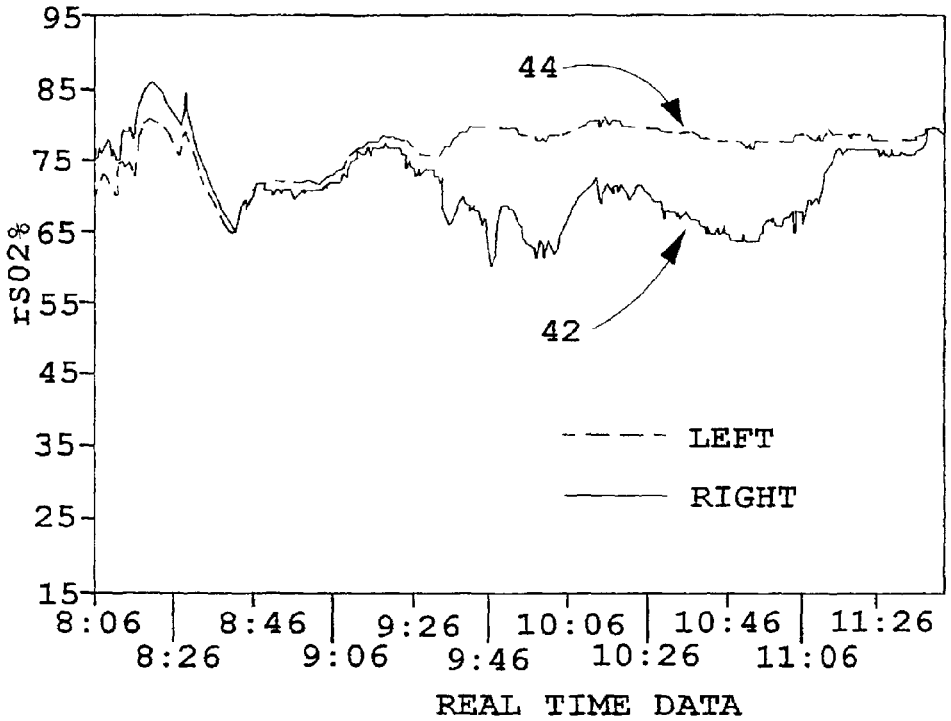

Graphic displays 42, 44 may also advantageously be arranged in the form shown in FIGS. 5, 6, and 7, in which the two such individual traces are directly superimposed upon one another, for more immediate and readily apparent comparison and contrast. Each of the examples shown in FIGS. 5, 6, and 7 does in fact represent the record from an actual surgical procedure in which the present invention was utilized, and in each of these the vertical axis (labeled $rSO_2$) is indicative of regional oxygen saturation values which have been determined, while the horizontal axis is, as labeled, "real time," i.e., ongoing clock time during the surgical procedure involved. The trace from the "left" sensor (number 16 as shown in FIGS. 1 and 3), designated by the numeral 42 for convenience, is shown in solid lines in these graphs, whereas the trace 44 from the right-hand sensor 116 is shown in dashed lines. The sensors may be placed on any region of their respective test areas (e.g., brain hemispheres) provided that any underlying hair is first removed, since hair is basically opaque to the applied light spectra and thus greatly reduces the amount of light energy actually introduced to the underlying tissue, etc.

Figure 4:
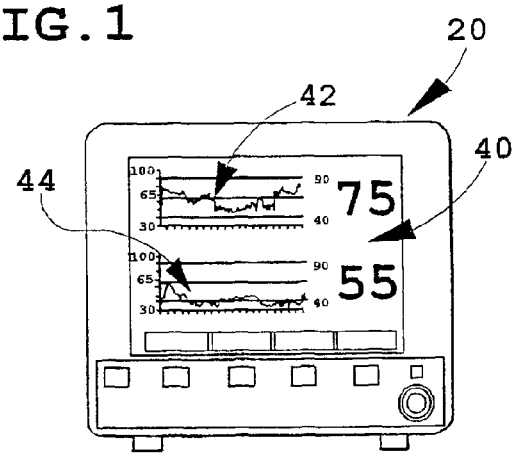
FIG. 4 is a front view of a typical control and processing unit for use in the invention, illustrating a preferred display of data determined in accordance with the invention.

With further reference to FIGS. 5, 6, and 7, and also inferentially to FIG. 4, it will be seen that at certain times, (e.g., the beginning and end of each procedure, when the patient's condition is at least relatively normal) there is a certain amount of direct correspondence between the two different hemispheric traces 42, 44, and that in at least these time increments the shape of the two traces is reasonably symmetrical and convergent. An idealized such normal result is shown in FIG. 1, wherein both the numeric values and the curves are basically the same. In each of the procedures shown in FIGS. 5, 6, and 7, however, there are times when the detected regional cerebral oxygen saturation differs markedly from one brain hemisphere to the other. This is particularly noticeable in FIG. 6, in which it may be observed that the left hand trace 42 is at times only about one half the height (i.e., value) of the right hand trace 44, reaching a minimal value in the neighborhood of about 35% slightly before real time point 12:21 as compared to the initial level, at time 10:50-11:00, of more than 75%, which is approximately the level of saturation in the right hemisphere at the 12:21 time just noted, when the oxygenation of the left hemisphere had decreased to approximately 35%.

As will be understood, the various differences in cerebral blood oxygenation shown by the superimposed traces of FIGS. 5, 6, and 7 occur as a result of measures taken during the corresponding surgical procedures, which in these cases are carotid endarterectomies and/or coronary artery bypass graft (CABG), which are sometimes undertaken as a continuing sequence. In the illustrated examples, FIG. 5 represents a sequential carotid endarterectomy and hypothermic CABG, in which the vertical lines along the time axis characterize certain events during surgery, i.e., index line 46 represents the time of the carotid arterial incision, line 48 represent the time the arterial clamp was applied and the shunt opened (resulting in reduced arterial blood flow to the left brain hemisphere), index line 50 represents a time shortly after the shunt was removed and the clamp taken off, and the area from about real time 17:43 to the end of the graph was when the hypothermic brain surgery actually took place, the lowest point (just prior to time 18:23) occurring when the heart-lung machine pump was turned on, and the indices at time 19:43 and 20:23 generally show the time for blood rewarming and pump off, respectively. While illustrative and perhaps enlightening, it is not considered necessary to give the specifics of the surgical procedures portrayed by the graphical presentations of FIGS. 6 and 7, although it may be noted that the procedure of FIG. 6 was a carotid endarterectomy of the left side and that of FIG. 7 was a similar endarterectomy on the right side of a different patient. Sufficient to say that these graphs represent other such surgical procedures and show comparable states of differing hemispheric oxygenation.

The importance and value of the information provided in accordance with the present invention is believed self-apparent from the foregoing, particularly the graphical presentations of and comments provided with respect to FIGS. 5, 6, and 7. Prior to the advent of the present invention, no such comparative or hemispheric-specific information was available to the surgeon, who did not in fact have any quantified or accurately representative data to illustrate the prevailing hemispheric brain oxygenation conditions during a surgery. Thus, even the use of a single such sensor (16, 116) on the side of the brain on which a procedure is to be done is highly useful and, as of the present time, rapidly being recognized as essential. Of course, it is considerably more useful to have at least the bilateral array illustrated in FIG. 1, to provide comparative data such as that seen in FIGS. 4-7 inclusive.

Figure 9:
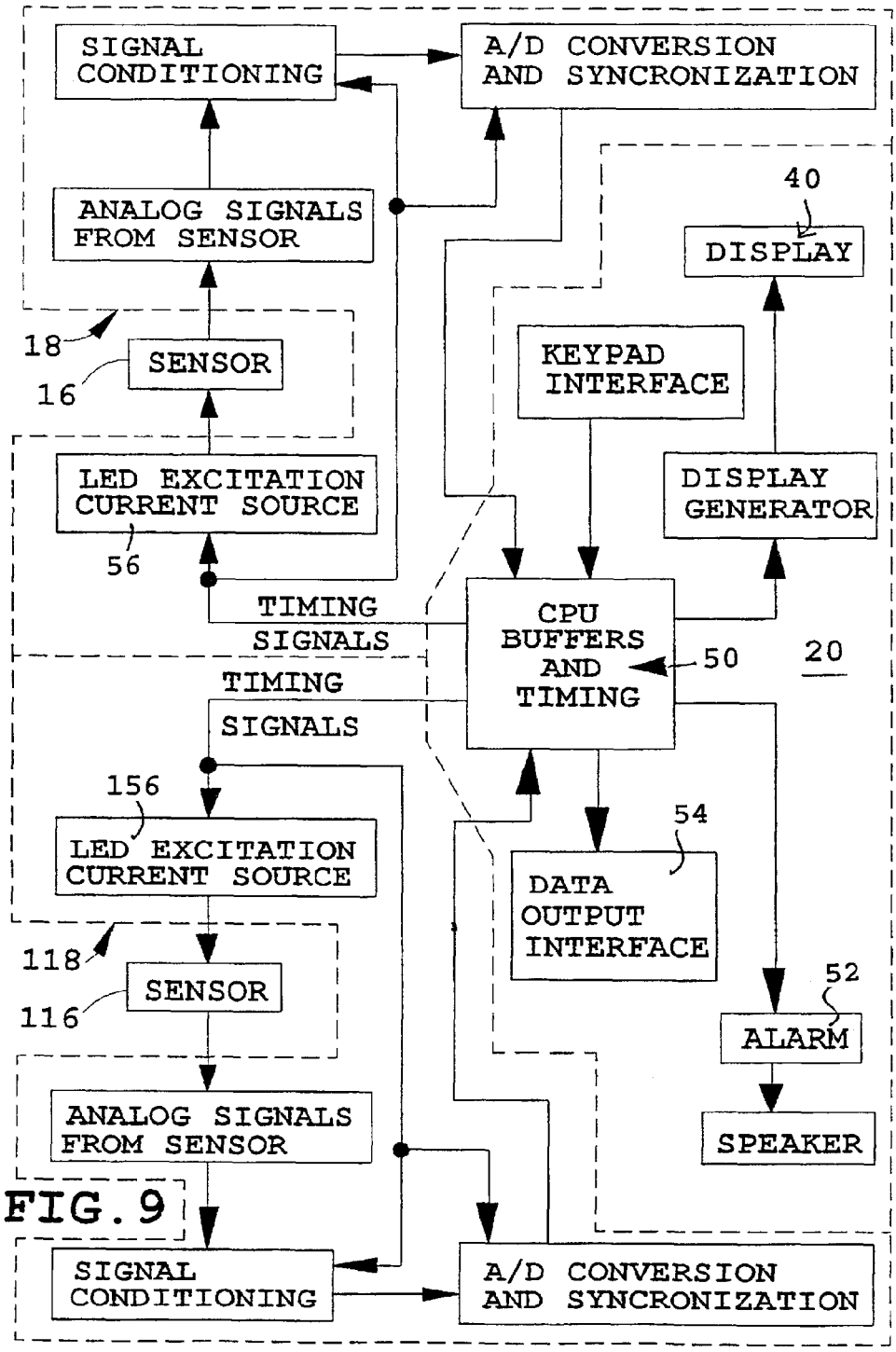
FIG. 9 is a schematic block diagram generally illustrating the componentry and system organization representative of a typical implementation of the invention; [and]

FIG. 9 is a schematic block diagram generally illustrating the componentry and system organization making up a typical implementation of the invention, as shown pictorially in FIG. 1 (to which reference is also made). As shown in FIG. 9, the oximeter 20 comprises a digital computer 50 which provides a central processing unit, with a processor, data buffers, and timing signal generation for the system, together with a keypad interface (shown along the bottom of the unit 20 in FIG. 1), display generator and display 40 (preferably implemented by use of a flat electro-luminescent unit, at least in applications where a sharp monochromatic display is sufficient), as well as an audible alarm 52 including a speaker, and a data output interface 54 by which the computer may be interconnected to a remote personal computer, disk drive, printer, or the like for downloading data, etc.

As also shown in FIG. 9, each of the sensors 16, 116 (and/or others, in the multi-site configuration illustrated in FIG. 8) receives timing signals from the CPU 50 and is coupled to an LED excitation current source (56,156) which drives the emitters 24 of each sensor. The analog output signals from the detectors (photodiodes) 26, 28 of each sensor are conveyed to the coupler/pre-amp 18, 118 for signal conditioning (filtering and amplification), under the control of additional timing signals from the CPU. Following that, these signals undergo A-to-D conversion and synchronization (for synchronized demodulation, as noted hereinafter), also under the control of timing signals from CPU 50, and they are then coupled to the CPU for computation of regional oxygen saturation $rSO_2$ data, storage of the computed data, and display thereof, preferably in the format discussed above in conjunction with FIGS. 4, 5, 6, and 7. As will be apparent, each sensor (16, 116, etc.) preferably has its own signal-processing circuitry (pre-amp, etc.) upstream of CPU 50, and each such sensor circuit is preferably the same.

While implementation of a system such as that shown in FIG. 9 is as a general matter well within the general skill of the art once the nature and purpose of the system and the basic requirements of its components, together with the overall operation (as set forth above and hereinafter) have become known, at least certain aspects of the preferred such system implementation are as follows. First, it is preferable that the light emitters 24 (i.e., LEDs) of each of the different sensors 16, 116 etc., be driven out-of-phase, sequentially and alternatingly with one another (i.e., only a single such LED or other emitter being driven during the same time interval, and the emitters on the respective different sensors are alternatingly actuated, so as to ensure that the detectors 26, 28 of the particular sensor 16, 116 then being actuated receive only resultant light spectra emanating from a particular emitter located on that particular sensor, and no cross-talk between sensors takes place (even though significant levels of cross-talk are unlikely in any event due to the substantial attenuation of light intensity as it passes through tissue, which is on the order of about ten times for each centimeter of optical path length through tissue). Further, it is desirable to carefully window the "on" time of the detectors 26, 28 so that each is only active during a selected minor portion (for example, 10% or less) of the time that the related emitter is activated (and, preferably, during the center part of each emitter actuation period). Of course, under computer control such accurate and intricate timing is readily accomplished, and in addition, the overall process may be carried on at a very fast rate.

Figure 10:
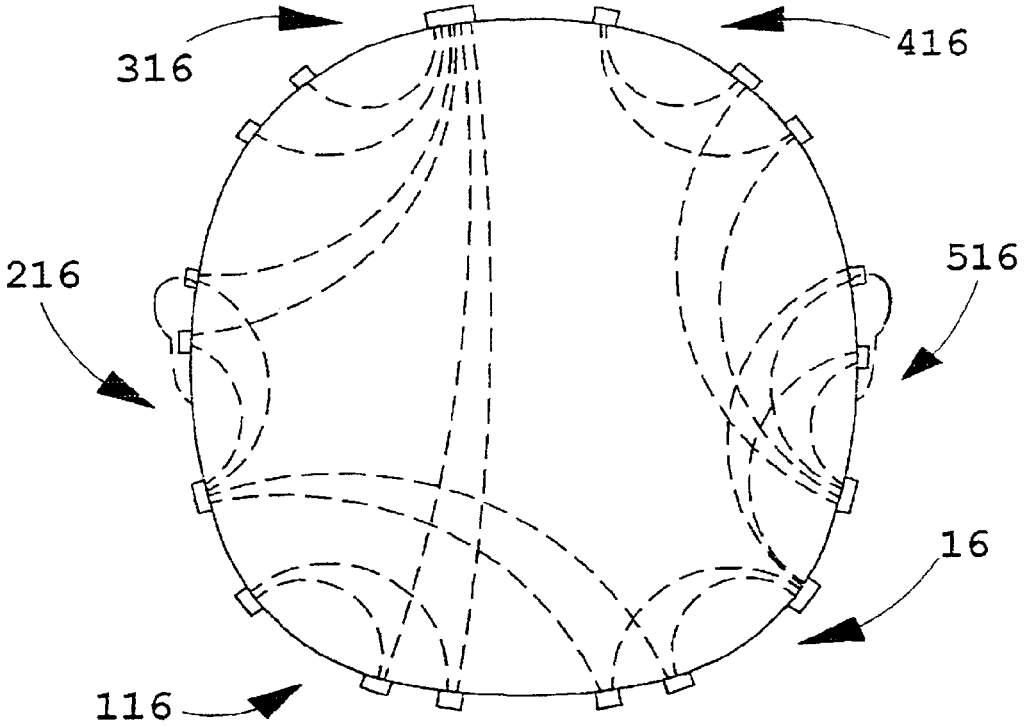
FIG. 10 is a pictorialized cross-sectional view similar to FIG. 8, but still further illustrating the multi-channel capability of the present invention[.]; *and*

In a multi-site (multiple sensor) system, such as that shown in FIG. 8, the preferred implementation and system operation would also be in accordance with that shown in FIG. 9, and the foregoing comments regarding system performance, data sampling, etc., would also apply, although there would of course be a greater number of sensors and sensor circuit branches interfacing with computer 50. The same would also be basically true of a single-source multi-site detector configuration or grouping such as that referred to above, taking into consideration the fact that the detectors would not necessarily be grouped in specific or dedicated "near-far" pairs and bearing in mind that one or more detectors located nearer a source than another detector, or detectors, located further from the source could be paired with or otherwise deemed a "near" detector relative to any such farther detector. In any such multiple-site configuration, it may be advantageous to implement a prioritized sequential emitter actuation and data detection timing format, in which more than one emitter may be operated at the same time, or some particular operational sequence is followed, with appropriate signal timing and buffering, particularly if signal cross-talk is not a matter of serious consideration due to the particular circumstances involved (detector location, size and nature of test subject, physiology, signal strength, etc.). As illustrated in FIG. 10, a multi-sensor or multiple sector-emitter array may be so operated, by using a number of different emitter-detector pair groupings, with some detectors used in conjunction with a series of different emitters to monitor a number of differing internal sectors or regions.

A system as described above may readily be implemented to obtain on the order of about fifteen data samples per second even with the minimal detector "on" time noted, and a further point to note is that the preferred processing involves windowing of the detector "on" time so that data samples are taken alternatingly during times when the emitters are actuated and the ensuing time when they are not actuated (i.e., "dark time"), so that the applicable background signal level may be computed and utilized in analyzing the data taken during the emitter "on" time. Other features of the preferred processing include the taking of a fairly large number (e.g., 50) of data samples during emitter "on" time within a period of not more than about five seconds, and processing that group of signals to obtain an average from which each updated $rSO_2$ value is computed, whereby the numeric value displayed on the video screen 40 is updated each five seconds (or less). This progression of computed values is preferably stored in computer memory over the entire length of the surgical procedure involved, and used to generate the graphical traces 42, 44 on a time-related basis as discussed above. Preferably, non-volatile memory is utilized so that this data will not be readily lost, and may in fact be downloaded at a convenient time through the data output interface 54 of CPU 50 noted above in connection with FIG. 9.

*As shown in FIGS. 11 and 12, a first emitter 624, a second emitter 626, a first detector 628, and a second detector 630 are placed over a first tissue region 632. The first emitter 624 is adapted to emit a first light into the first tissue region 632 and the second emitter 626 is adapted to emit a second light into the first tissue region 632. The first detector 628 is located a first distance 634, also referred to as the first line 634, from the first emitter 624 and is located a second distance 636, also referred to as the second line 636, from the second emitter 626. As shown in these figures, the second distance 636 is greater than the first distance 634. The second detector 630 is located a third distance 638, also referred to as the third line 638, from the first emitter 624 and is located a fourth distance 640, also referred to as the fourth line 640, from the second emitter 626. As shown in these figures, the fourth distance 640 is less than the third distance 638. The first emitter 624 is closer to the first detector 628 than the second detector 630, and the second emitter 626 is closer to the second detector 630 than the first detector 628. The third distance 638 is longer than the first distance 634 and is longer than the fourth distance 640. The second distance 636 is approximately equal to the third distance 638. The first distance 634 is approximately equal to the fourth distance 640.*

*As further shown in FIGS. 11 and 12, the first emitter 624, the second emitter 626, the first detector 628 and the second detector 630 are aligned within the cross-sectional plane. In addition, the second line 636 defined between the center of the first detector 628 and the center of the second emitter 626 partially overlaps with the third line 638 defined between the center of the second detector 630 and the center of the first emitter 624.*

*Referring now to FIG. 11, a third emitter 724, a fourth emitter 726, a third detector 728, and a fourth detector 730 are placed over a second tissue region 732. The third emitter 724 is adapted to emit a third light into the second tissue region 732 and the fourth emitter 726 is adapted to emit a fourth light into the second tissue region 732. The third detector 728 is located a fifth distance 734, also referred to as the fifth line 734, from the third emitter 724 and is located a sixth distance 736, also referred to as the sixth line 736, from the second emitter 726. The second detector 730 is located a seventh distance 738, also referred to as the seventh line 738, from the third emitter 724 and is located an eighth distance 740, also referred to as the eighth line 740, from the fourth emitter 726. As also shown in FIG. 11, the third emitter 724 is closer to the third detector 728 than the fourth detector 730, and the fourth emitter 726 is closer to the fourth detector 730 than the third detector 728. The fifth distance 734 is less than the seventh distance 738. The eighth distance 740 is less than the sixth distance 736.*

*As shown in FIGS. 13 and 14, the first detector 628 is adapted to detect the first light propagated over a first mean path 664 through the first tissue region 632 and to detect the second light propagated over a second mean path 666 through the first tissue region 632. The second mean path 666 has a length 667 greater than a length 665 of the first mean path 664. The second detector 630 is adapted to detect the first light propagated over a third mean path 668 through the first tissue region 632 and is adapted to detect the second light*

*propagated over a fourth mean path 670 through the first tissue region 632. The fourth mean path 670 has a length 671 less than the length 669 of the third mean path 668. The length 665 of the first mean path 664 is substantially equivalent to the length 671 of the fourth mean path 670 and the length 669 of the third mean path 668 is substantially equivalent to the length 667 of the second mean path 666. The length 665 of the first mean path 664 is less than the length 669 of the third mean path 668 and the length 671 of the fourth mean path 670 is less than the length 667 of the second mean path 666. The second mean path 666 and the third mean 668 path overlap at a location 672 below a tissue surface of the tissue region 632. In addition, along a line 674 orthogonal to the surface of the tissue between the first detector 628 and the second detector 630, the third mean path 668 lies farther from the tissue surface than the second mean path 666. The second mean path 666 lies substantially as far from a tissue surface as the third mean path 668 at approximately a midpoint 676 between the first detector 628 and the second detector 630.*

*As further shown in FIGS. 13 and 14, the first emitter 624 and the first detector 628 form a first near coupling. The second detector 630 is located farther from the first emitter 624 than the first detector 628 to form a first far coupling. The second emitter 626 and the first detector 628 form a second far coupling. The second detector 630 is located closer to the second emitter 626 than the first detector 628 to form a second near coupling. The first emitter 624 is adapted to transmit the first light along the first mean path 664 through a first section 680 of the first tissue region 632. The second emitter 626 is adapted to transmit the second light along the second mean path 666 through the first section 680 of the first tissue region 632 and the fourth mean path 670 through a second section 682 of the first tissue region 632. The first emitter is adapted to transmit the first light along the third mean path 668 through the second section 682 of the first tissue region 632. The first emitter 624 and the second emitter 626 are further adapted to transmit the first light and the second light along the third mean path 668 and second mean path 666, respectively, through a third section 684 of the first tissue region 632 and to transmit the first light and the second light along the first mean path 664 and the fourth mean path 670, respectively, that substantially avoid the third section 684 of the first tissue region 632.*

*As shown in FIG. 13, the third detector 728 is adapted to detect the third light propagated over a fifth mean path 764 through the second tissue region 732. The third detector 728 is adapted to detect the fourth light propagated over a sixth mean path 766 through the second tissue region 732. The fourth detector 730 is adapted to detect the third light propagated over a seventh mean path 768 through the second tissue region 732. The fourth detector 730 is adapted to detect the fourth light propagated over an eighth mean path 770 through the second tissue region 732. The length 769 of the seventh mean path 768 is greater than the length 765 of the fifth mean path 764 and the length 767 of the sixth mean path 766 is greater than the length 771 of the eighth mean path 770.*

*As shown in FIG. 15, a first transmitter 724 (previously referred to as the third emitter 724 during the discussion of FIGS. 11 and 13 above), a first detector 826, a second detector 828, and a third detector 830 are placed over a first region of tissue 732 (previously referred to as the second tissue region 732 during the discussion of FIGS. 11 and 13 above). The first transmitter 724 is adapted to transmit light into the first region of tissue 732. The first detector 826 forms a near detector grouping with the first transmitter 724. The second detector 828 and the third detector 830 are located farther from the first transmitter 724 than the first detector 826 to form far detector groupings. As also shown in FIG. 15, a line 840 passing through a midpoint of the first transmitter 724 and a midpoint of the first detector 826 is spaced apart from a midpoint of the second detector 828 and a midpoint of the third detector 830. In addition, the line 840 defined between a center of the first transmitter 724 and the center of the first detector 826 forms an acute angle 842 with a line 844 defined between the center of the transmitter 724 and a center of the second detector 828. The line 840 defined between the center of the first transmitter 724 and the center of the first detector 826 forms a second acute angle 846 with a line 848 defined between the center of the transmitter 724 and a center of the third detector 830, with the second acute angle 846 substantially similar to the first acute angle 842.*

*As further shown in FIG. 15, a second transmitter 624 (previously referred to as the first emitter 624 during the discussion of FIGS. 11-14 above), a fourth detector 628 (previously referred to as the first detector 628 during the discussion of FIGS. 11-14 above), a fifth detector 928, and a sixth detector 930 are placed over a second region of tissue 632 (previously referred to as the first tissue region 632 during the discussion of FIGS. 11-14 above). The fourth detector 628 forms a near detector grouping with the second transmitter 624. The fifth detector 928 and the sixth detector 930 are each located farther from the second transmitter 624 than the fourth detector 628 to form far detector groupings. As shown in FIG. 15, the distance 940 between the first transmitter 724 and the first detector 826 is approximately equal to the distance 942 between the second transmitter 624 and the fourth detector 628.*

As will be understood, the foregoing disclosure and attached drawings are directed to a single preferred embodiment of the invention for purposes of illustration; however, it should be understood that variations and modifications of this particular embodiment may well occur to those skilled in the art after considering this disclosure, and that all such variations etc., should be considered an integral part of the underlying invention, especially in regard to particular shapes, configurations, component choices and variations in structural and system features. Accordingly, it is to be understood that the particular components and structures, etc. shown in the drawings and described above are merely for illustrative purposes and should not be used to limit the scope of the invention, which is defined by the following claims as interpreted according to the principles of patent law, including the doctrine of equivalents.

The invention claimed is:

[1. A method for comparative spectrophotometric in vivo monitoring and display of selected blood metabolites present in a plurality of different internal regions of the same test subject on a continuing and substantially concurrent basis, comprising the steps of:

applying separate spectrophotometric sensors to a test subject at each of a plurality of separate testing sites and coupling each of said sensors to a control and processing station;

operating a selected number of said sensors on a substantially concurrent basis to spectrophotometrically irradiate at least two separate internal regions of the test subject during a common time interval, each of said regions being associated with a different of said testing sites;

separately detecting and receiving light energy resulting from said spectrophotometric irradiation for each of said at least two separate internal regions, and conveying separate sets of signals to said control and processing station which correspond to the separately detected light energy from said at least two separate internal regions;

separately and concurrently analyzing said conveyed separate sets of signals to separately determine quantified data representative of a blood metabolite in each of said at least two separate internal regions; and concurrently visually displaying said separately determined quantified data for each of said at least two separate internal regions for direct concurrent mutual comparison, wherein said sensors are applied to a head of the test subject and are used to monitor two mutually separate regions within a brain of the test subject.]

[2. The method of claim 1, wherein said step of analyzing comprises quantitative determination of blood oxygenation levels within each of said at least two separate internal regions.]

[3. The method of claim 2, wherein said analyzing step includes producing separate quantitative value determinations for hemoglobin oxygen saturation for each of said at least two separate internal regions.]

[4. The method of claim 3, wherein said analyzing step includes production of ongoing graphical traces representing a plurality of said quantitative value determinations made at successive points in time.]

[5. The method of claim 4 including the step of visually displaying a plurality of said graphical traces at substantially the same time and in predetermined relationship to one another to facilitate rapid and accurate visual comparison.]

[6. The method of claim 5, including the step of visually displaying a plurality of said quantitative value determinations at substantially the same time and in predetermined relationship to one another to facilitate rapid and accurate visual comparison.]

[7. The method of claim 3, including the step of visually displaying a plurality of said quantitative value determinations at substantially the same time and in predetermined relationship to one another to facilitate rapid and accurate visual comparison.]

[8. The method of claim 1, wherein said metabolite comprises hemoglobin oxygen.]

[9. The method of claim 1, wherein said sensors are positioned in locations proximate to different brain hemispheres and said two mutually separate regions are located in a different brain hemisphere.]

[10. The method of claim 9, wherein said metabolite comprises cerebral blood hemoglobin oxygenation.]

[11. An apparatus for concurrent comparative spectrophotometric in vivo monitoring of selected blood metabolites present in each of a plurality of different internal regions on a continuing basis, comprising:

a plurality of spectrophotometric sensors, each attachable to a test subject at different test locations and adapted to separately but concurrently spectrophotometrically irradiate at least two different internal regions within the test subject associated with each of said test locations;

a controller and circuitry coupling each of said sensors to said controller for separately and individually but concurrently operating certain of said sensors to spectrophotometrically irradiate each of said different internal regions within the test subject associated with each of said test locations;

said sensors each further adapted to receive light energy resulting from the separate spectrophotometric irradiation of said sensors' associated one of said at least two different internal regions on a substantially concurrent basis with other said sensors, and to produce separate signals corresponding to the light energy received, said circuitry acting to convey said separate signals to said controller for separate analytic processing;

said controller adapted to analytically process said conveyed signals separately and determine separate quantified blood metabolite data therefrom for each of said sensors and said sensors' associated one of said at least two different internal regions; and a visual display coupled to said controller and adapted to separately but concurrently display the quantified blood metabolite data determined for each of said sensors in a mutually-comparative manner, wherein said sensors are adapted to be applied to a head of the test subject and to monitor a brain of the test subject.]

[12. The apparatus of claim 11, wherein said controller is adapted to analyze said data to quantitatively determine blood oxygenation within said at least two different internal regions.]

[13. The apparatus of claim 12, wherein said controller is adapted to produce separate numeric value designations for hemoglobin oxygen saturation for said at least two different internal regions.]

[14. The apparatus of claim 13, wherein said controller and said display are adapted to produce ongoing graphical traces representing a plurality of said numeric value designations for the same region taken over a period of time.]

[15. The apparatus of claim 14, wherein said controller and said display are adapted to visually display at least two of said graphical traces on a substantially concurrent basis and in predetermined relationship to one another to facilitate rapid and accurate visual comparison.]

[16. The apparatus of claim 15, wherein said controller and said display are adapted to visually display at least two of said numeric value designations as well as at least two of said graphical traces on a substantially concurrent basis and in proximity to one another to facilitate rapid and accurate visual comparison.]

[17. The apparatus of claim 13, wherein said controller and said display are adapted to visually display at least two of said numeric value designations on a substantially concurrent basis and in predetermined relationship to one another to facilitate rapid and accurate visual comparison.]

[18. The apparatus of claim 11, wherein said sensors are adapted to provide signals to said controller which comprise at least two separate data sets that cooperatively define at least portions of a particular area within a given one of said at least two different internal regions.]

[19. The apparatus of claim 18, wherein said data sets provided by said sensors include a first set characterizing a first part of said particular area and a second set characterizing a second part of said particular area.]

[20. The apparatus of claim 19, wherein said second part of said particular area characterized by said second set includes at least part of said first part of said area.]

[21. The apparatus of claim 11, wherein said controller is adapted to determine blood oxygenation saturation in said brain.]

[22. The apparatus of claim 11, wherein at least two of said sensors are adapted to be positioned in locations associated with mutually different hemispheres of the brain and each of said sensors is operable to separately monitor at least portions of each of said different hemispheres.]

[23. The apparatus of claim 22, wherein said controller is adapted to determine cerebral blood oxygenation saturation within each of said different hemispheres.]

[24. The apparatus of claim 22, wherein said sensors are adapted to provide signals to said controller which comprise at least two data sets that cooperatively define at least portions of a particular area within the same hemisphere of said brain.]

[25. The apparatus of claim 11, wherein said sensors are adapted to be applied to the outside periphery of the test subject and to operate non-invasively.]

[26. A method for concurrent comparative in vivo monitoring of blood metabolites in each of a plurality of different internal regions in a selected test subject, comprising the steps of:

spectrophotometrically irradiating each of a plurality of different testing sites on said test subject;

detecting light energy resulting from said spectrophotometric irradiation of said testing sites, and providing separate sets of signals to a control and processing station which are representative of the light energy received by each of said testing sites and which cooperatively define blood metabolite data for an individual one of at least two different internal regions;

analyzing said separate signals to determine quantified blood metabolite data representative of at least one defined region within said at least one test subject associated with each of at least two different of said testing sites, each said defined region being different from the other; and concurrently displaying data sets for each of said at least two different internal regions at substantially the same time for direct mutual comparison, wherein said at least two different internal regions are located within different brain hemispheres of said test subject.]

[27. The method of claim 26, wherein said data sets include a first set which characterizes a first zone within one of said at least two different internal regions and a second set which characterizes a second zone that is at least partially within the same one of said at least two different internal regions.]

[28. The method of claim 26, wherein said spectrophotometric irradiation comprises application of at least two different wavelengths applied in an alternating sequence of timed pulses, and wherein detection of light energy corresponding to each of said at least two different wavelengths is done on a timed periodic basis using detection periods whose occurrence generally corresponds to that of said applied spectrophotometric irradiation.]

[29. The method of claim 28, wherein the duration of each of said detection periods is limited to a length which is less than that of each pulse of applied spectrophotometric irradiation.]

[30. The method of claim 29, wherein the duration of each of said detection periods is less than half that of a pulse of said applied spectrophotometric irradiation.]

[31. The method of claim 30, wherein a plurality of said detection periods are used during pulses of said applied spectrophotometric irradiation, and a corresponding energy detection occurs during each of a plurality of said detection periods.]

[32. The method of claim 31, further including the steps of averaging a selected number of energy detection event values to obtain a resultant value therefor, and using said resultant value to compute a metabolite value which is representative thereof.]

[33. The method of claim 32, wherein said display includes said computed representative metabolite value.]

[34. The method of claim 33, wherein said display is refreshed periodically by using a sequence of computed representative metabolite values which are based upon and represent the averaged detection event values produced during the different time intervals corresponding to the intervals of said periodic display refreshment.]

[35. Apparatus for spectrophotometric in vivo monitoring of a selected metabolic condition in each of a plurality of different test subject regions on a substantially concurrent basis, comprising:

a plurality of spectrophotometric emitters, each adapted to separately spectrophotometrically irradiate a designated region within a test subject from a test location on said test subject;

a controller and circuitry coupling each of said emitters to said controller for individually operating selected ones of said emitters to spectrophotometrically irradiate at least two particular regions within the test subject;

a plurality of detectors, each adapted to separately receive light energy resulting from the spectrophotometric irradiation of said at least two particular regions, and to produce at least one separate set of signals for each one of said at least two particular regions; and circuitry acting to convey said at least one separate set of signals to said controller for analytic processing;

said controller adapted to analytically process said at least one separate set of signals to determine separate sets of quantified data representative of a metabolic condition in said at least two particular regions; and a visual display coupled to said controller and adapted to display separate representations of said separate sets of quantified data for each of said at least two particular regions in a mutually-comparative manner and on a substantially concurrent basis, wherein at least two of said at least two particular regions are located in mutually separate regions of a brain of said test subject.]

[36. The apparatus of claim 35, wherein said controller includes a computer programmed to analyze said signals to separately determine a blood oxygenation state within each of said at least two particular regions.]

[37. The apparatus of claim 36, wherein said computer comprises a processor, data buffers, and a timing signal generator, said data buffers adapted to store data representative of said blood oxygenation state and said timing signal generator adapted to control actuation of said emitters and detectors.]

[38. The apparatus of claim 36, wherein said controller comprises a unitary device which includes said computer and said display.]

[39. The apparatus of claim 38, wherein said unitary device further includes a keyboard interface to said computer.]

[40. The apparatus of claim 38, wherein said unitary device further includes a data output interface.]

[41. The apparatus of claim 40, wherein said unitary device further includes an integral keyboard interface to said computer.]

[42. The apparatus of claim 38, wherein said display comprises a flat electroluminescent visual display screen.]

[43. The apparatus of claim 42, wherein said unitary device further includes an integral keyboard interface to said computer.]

[44. The apparatus of claim 35, wherein at least certain of said detectors and certain of said emitters comprise operational pairs, and said controller is arranged to operate the emitters and detectors of at least certain of said operational pairs in predetermined timed relationship while maintaining the emitters and detectors of other of said operational pairs in a non-operating condition.]

[45. The apparatus of claim 44, wherein said controller is adapted to sequence the operation of said at least certain of said operational pairs.]

[46. The apparatus of claim 45, wherein at least one of said operational pairs include a plurality of said detectors arranged at mutually spaced locations which are spaced at differing distances from the emitter of said at least one of said operational pairs.]

[47. The apparatus of claim 46, wherein said controller is adapted to operate the emitter and a selected number less than all of the detectors of at least one of said operational pairs substantially in unison while holding the other detectors of said at least one of said operational pairs in a non-operating condition, and said controller is further arranged to operate said other detectors substantially in unison with said emitter at another time during which said selected number of said detectors are maintained in a non-operating condition.]

[48. The apparatus of claim 44, wherein at least one of said operational pairs includes a first detector and a second detector, and wherein the first detector is located nearer the emitter than the second detector to thereby provide near and far detector groupings for said at least one of said operational pairs.]

[49. The apparatus of claim 48, wherein said controller is adapted to sequence the operation of said at least one of said operational pairs.]

*50. A system for evaluating oxygen saturation levels in a region of human tissue, the system comprising:*

*a first emitter, a second emitter, a first detector, and a second detector, the first emitter being adapted to emit at least a first light into the tissue region, the second emitter being adapted to emit at least a second light into the tissue region;*

*the first detector being located a first distance from the first emitter and a second distance from the second emitter greater than the first distance, the first detector being further configured to detect at least two different wavelengths of the first light and at least two different wavelengths of the second light;*

*the second detector being located a third distance from the first emitter and a fourth distance from the second emitter less than the third distance, the second detector being further configured to detect at least two different wavelengths of the first light and at least two different wavelengths of the second light;*

*the first detector and the second detector being configured to produce a set of signals indicative of the first light and the second light detected by the first detector and the second detector; and*

*an oximeter unit configured to reduce cross-talk between the first emitter and the second emitter by driving the first emitter and the second emitter in sequence on a substantially simultaneous basis, the oximeter unit further configured to receive the set of signals and to determine at least a regional blood oxygen saturation value for the tissue region based at least in part on the set of signals.*

*51. The system of claim 50, wherein the first emitter, the second emitter, the first detector, and the second detector are aligned within a plane.*

*52. The system of claim 50, wherein a line defined between a center of the first detector and a center of the second emitter partially overlaps with a line defined between a center of the second detector and a center of the first emitter.*

*53. The system of claim 50, wherein the third distance is longer than the first distance and is longer than the fourth distance.*

*54. The system of claim 50, wherein the second distance is approximately equal to the third distance.*

*55. The system of claim 54, wherein the first distance is approximately equal to the fourth distance.*

*56. The system of claim 50, wherein the first and second emitters alternately emit the first light and the second light along a paring of mean paths.*

*57. The system of claim 50, wherein the oximeter unit is capable of removing one or more effects attributable to portions of the tissue region through which the first light propagates before being detected by the first detector and through which the second light propagates before being detected by the second detector.*

*58. The system of claim 50, wherein the first light and the second light each include at least four different wavelengths and wherein the first detector and the second detector are adapted to detect each of the four different wavelengths.*

*59. The system of claim 50, wherein the first emitter comprises:*

*a first narrow-bandwidth light-emitting diode (LED) configured to output a first center output wavelength of the first light;*

*a second narrow-bandwidth LED configured to output a second center output wavelength of the first light, the second center output wavelength being different than the first center output wavelength;*

*a third narrow-bandwidth LED configured to output a third center output wavelength of the first light, the third center output wavelength being different than the first center output wavelength and the second center output wavelength; and*

*a fourth narrow-bandwidth LED configured to output a fourth center output wavelength of the first light, the fourth center output wavelength being different than the first, second, and third center output wavelengths, wherein the first detector and the second detector are adapted to detect each of the four center output wavelengths of the first light.*

*60. The system of claim 50, wherein the tissue region is a first tissue region, the set of signals is a first set of signals, and the regional blood oxygen saturation value is a first regional blood oxygen saturation value, the system further comprising a third emitter, a fourth emitter, a third detector, and a fourth detector, the third emitter being adapted to emit at least a third light into a second tissue region, the fourth emitter being adapted to emit at least a fourth light into the second tissue region;*

*the third detector being located a fifth distance from the third emitter and a sixth distance from the fourth emitter, the third detector being further configured to detect at least two different wavelengths of the third light and at least two different wavelengths of the fourth light;*

*the fourth detector being located a seventh distance from the third emitter and an eighth distance from the fourth emitter, the fourth detector being configured to detect at least two different wavelengths of the third light and at least two different wavelengths of the fourth light;*

*the third emitter being closer to the third detector than the fourth detector and the fourth emitter being closer to the fourth detector than the third detector;*

*the third detector and the fourth detector being configured to produce a second set of signals indicative of the third light and fourth light detected by the third detector and the fourth detector; and*

*the oximeter unit being configured to reduce cross-talk between the third emitter and the fourth emitter by driving the third emitter and the fourth emitter in sequence on a substantially simultaneous basis, the oximeter unit further configured to receive the second set of signals and to determine at least a second regional blood oxygen*

*saturation value for the second tissue region based at least in part on the second set of signals.*

*61. The system of claim 60, wherein the oximeter unit includes a display configured to convey one or more superimposed trace lines indicative of at least the first regional blood oxygen saturation value and the second regional blood oxygen saturation value.*

*62. The system of claim 60, wherein the first and second emitters are adapted to emit the first and second light, respectively, into a first brain hemisphere, the third and fourth emitters are adapted to emit the third and fourth light, respectively, into a second brain hemisphere, and the oximeter unit is capable of determining a regional blood oxygen saturation value of the first brain hemisphere and determining a regional blood oxygen saturation value of the second brain hemisphere.*

*63. The system of claim 50, wherein the first emitter and the first detector form a first near coupling, the second detector is separated from the first emitter by a distance that is greater than a distance between the first emitter and the first detector to form a first far coupling, the second emitter and the first detector form a second far coupling, and the second detector is separated from the second emitter by a distance that is less than a distance between the first emitter and the second detector to form a second near coupling.*

*64. The system of claim 50, wherein a distance between the first detector and the second detector is approximately equal to the first distance and to the fourth distance.*

*65. The system of claim 50, wherein the first detector is adapted to produce signals indicative of background light during a time that the first and second emitters are not emitting, and the oximeter unit is further configured to determine the regional blood oxygen saturation value using the signals indicative of the background light.*

*66. The system of claim 50, wherein the first emitter and the second emitter are secured within different sensor bodies.*

*67. A method for evaluating oxygen saturation levels in a region of human tissue, the method comprising:*

*detecting, with a first detector, at least two different wavelengths of a first light propagated from a first emitter into the human tissue region and at least two different wavelengths of a second light propagated from a second emitter into the human tissue region, the first emitter and the second emitter emitting light sequentially and alternatingly with one another on a substantially simultaneous basis;*

*detecting, with a second detector, at least two different wavelengths of the first light propagated from the first emitter into the human tissue region and at least two different wavelengths of the second light propagated from the second emitter into the human tissue region;*

*the first emitter being closer to the first detector than the second detector and the second emitter being closer to the second detector than the first detector;*

*generating, with the first and second detectors, a set of signals indicative of the first light and the second light detected by the first detector and the second detector;*

*receiving, with an oximeter unit, the set of signals; and*

*determining, with the oximeter unit, at least a regional blood oxygen saturation value for the human tissue region based at least in part on the set of signals.*

*68. The method of claim 67, wherein the human tissue region is a first human tissue region, the set of signals is a first set of signals, and the regional blood oxygen saturation value is a first regional blood oxygen saturation value, the method further comprising steps of:*

*detecting, with a third detector, at least two different wavelengths of a third light propagated from a third emitter into a second human tissue region and at least two different wavelengths of a fourth light propagated from a fourth emitter into the second human tissue region;*

*detecting, with a fourth detector, at least two different wavelengths of the third light propagated from the third emitter into the second human tissue region and at least two different wavelengths of the fourth light propagated from the fourth emitter into the second human tissue region, the third emitter and the fourth emitter emitting light sequentially and alternatingly with one another on a substantially simultaneous basis;*

*the third emitter being closer to the third detector than the fourth detector and the fourth emitter being closer to the fourth detector than the third detector;*

*generating, with the third and fourth detectors, a second set of signals associated with the third light and the fourth light detected by the third detector and the fourth detector;*

*receiving, with an oximeter unit, the second set of signals; and*

*determining, with the oximeter unit, at least a second regional blood oxygen saturation value for the second human tissue region based at least in part on the second set of signals.*

*69. The method of claim 68, further comprising a step of displaying a first indicator of the first regional blood oxygen saturation value on a monitor of the oximeter unit and a step of displaying a second indicator of the second regional blood oxygen saturation value on the monitor.*

*70. The method of claim 68, wherein the step of determining, at the oximeter unit, at least the first regional blood oxygen saturation value includes removing one or more effects attributable to a portion of the human tissue in which the first light propagates before being detected by the first detector.*

*71. The method of claim 70, wherein the step of determining, at the oximeter unit, at least the second regional blood oxygen saturation value includes removing one or more effects attributable to a portion of the human tissue through which the third light propagates before being detected by the third detector and through which the fourth light propagates before being detected by the fourth detector.*

*72. The method of claim 67, wherein the first light detected at the first detector includes a first center output wavelength, a second center output wavelength, a third center output wavelength, and a fourth center output wavelength, each of the four center output wavelengths being different from the other three center output wavelengths and each center output wavelength being generated by a separate narrow-bandwidth light-emitting diode.*

* * * * *